United States Patent
Nadal et al.

(10) Patent No.: US 6,620,201 B1
(45) Date of Patent: Sep. 16, 2003

(54) ONE PIECE MEDICAL PROSTHESIS FOR AN ANATOMICAL DUCT

(75) Inventors: Guy Nadal, Poitiers (FR); Maurice Roussigne, Poitiers (FR)

(73) Assignee: B. Braun Medical, Boulogne-Billancourt (FR)

(*) Notice: Subject to any disclaimer, the term of this patent is extended or adjusted under 35 U.S.C. 154(b) by 0 days.

(21) Appl. No.: 09/680,533

(22) Filed: Oct. 6, 2000

(30) Foreign Application Priority Data

Oct. 19, 1999 (FR) .............................. 99 12630

(51) Int. Cl.$^7$ .................................................. A61F 2/04
(52) U.S. Cl. ...................................... 623/23.7; 623/1.15
(58) Field of Search ............................ 623/1.15–1.18, 623/1.2, 1.22, 23.7; 606/195

(56) References Cited

U.S. PATENT DOCUMENTS

| | | | | | |
|---|---|---|---|---|---|
| 5,776,183 | A | * | 7/1998 | Kanesaka et al. | 623/23.7 |
| 5,807,404 | A | * | 9/1998 | Richter | 623/23.7 |
| 5,810,872 | A | * | 9/1998 | Kanesaka et al. | 623/23.7 |
| 5,911,754 | A | * | 6/1999 | Kanesaka et al. | 623/23.7 |
| 5,913,895 | A | * | 6/1999 | Burpee et al. | 623/23.7 |
| 5,922,021 | A | * | 7/1999 | Jang | 623/23.7 |
| 5,964,798 | A | * | 10/1999 | Imran | 623/23.7 |
| 6,033,433 | A | * | 3/2000 | Ehr et al. | 623/23.7 |
| 6,042,597 | A | * | 3/2000 | Kveen et al. | 623/23.7 |
| 6,066,169 | A | * | 5/2000 | McGuinness | 623/23.7 |
| 6,129,754 | A | * | 10/2000 | Kanesaka et al. | 623/1 |

FOREIGN PATENT DOCUMENTS

| | | |
|---|---|---|
| EP | 0884029 | 12/1998 |
| FR | 2774278 | 8/1999 |
| WO | 9840035 | 9/1998 |
| WO | 9842277 | 10/1998 |

* cited by examiner

*Primary Examiner*—David H. Willse
*Assistant Examiner*—Javier G. Blanco
(74) *Attorney, Agent, or Firm*—Rothwell, Figg, Ernst & Manbeck (57) ABSTRACT

A medical prosthesis implantable in an anatomical duct in order to treat a disease of the duct, the prosthesis having a longitudinal axis, a first radially restricted state or a second radially expanded state, a proximal end and a distal end, first structural elements having meanders extending along a series of parallel helices coiled around the longitudinal axis, the meanders having apices alternately directed towards the proximal end and the distal end, and second structural discrete elements extending along a series of parallel lines perpendicular to the longitudinal axis, the second structural discrete elements being individually arranged between two adjacent first structural elements and defining connecting struts by intersecting the two adjacent first structural elements, the second structural discrete elements showing changes of slope with at least one shoulder, but not apices.

6 Claims, 9 Drawing Sheets

ONE PIECE MEDICAL PROSTHESIS FOR AN ANATOMICAL DUCT

BACKGROUND OF THE INVENTION

1. Field of the Invention

The invention is related to a one-piece medical prosthesis implantable in an anatomical duct in order to treat a disease of said duct.

2. Description of the Related Art

The prosthesis has a longitudinal axis a first radially restricted state or a second radially expanded state and a proximal end and a distal end.

Such a prosthesis is also called a "stent".

Figure 1:
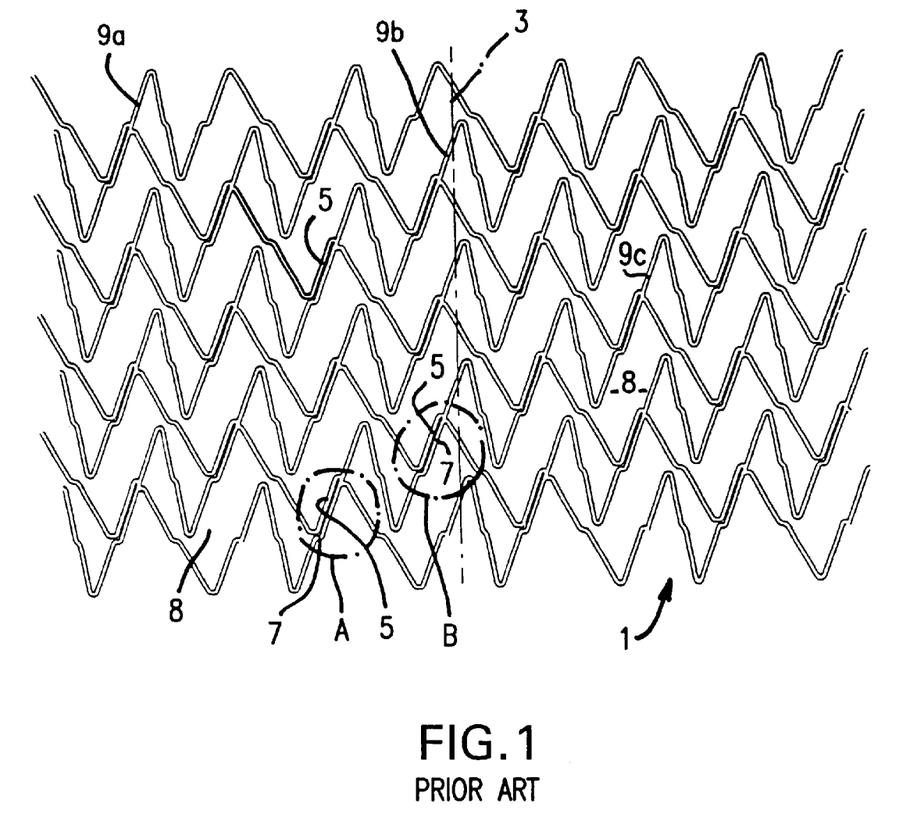
FIG. 1 shows a flat expanded view of the structure of a prosthesis such as known in prior art.

On FIG. 1, an example of such a prosthesis is shown as an example of prior art stent.

On this FIG. 1, a portion of a tubular wall structure of a medical intravascular prosthesis 1 is illustrated in a flat expanded view.

This illustration shows said structure as shaped when the prosthesis is in its radially expanded state. The axis 3 materializes the longitudinal direction of the prosthesis around which the prosthesis extends along a cylinder tube.

It can be noticed at 5 that a section of said structure extends near and substantially parallel to another section 7, in the way of a double thread line. This particularity can be seen in different zones such as those referenced A and B on said figure.

This doubling is an inconvenient insofar as meanders substantially "zigzag"-shaped, such as 9a, 9b, and 9c, look "warped". In other words, in its expanded state, the structure of said prosthesis shows a non-regular aspect. In addition, existence of sections 5 and 7 leads to a rigidity of the upper part of the stent at about these "doubled sections". The global balance of the prosthesis may suffer therefrom. The warping implied by this "doubling" on the cells 8 of the prosthesis may affect both the reliability of the opening, the mechanical characteristics and even the efficiency of the prosthesis as a whole.

For bringing a solution to this problem and improving the global quality of the prosthesis, the invention points out modifications which may be set out in three different ways which have in common to solve the above-mentioned drawbacks.

SUMMARY OF THE INVENTION

First, it can be stated that the invention points out to modify the above-described prosthesis so that it shows:

first structural elements having meanders extending along a series of parallel helices coiled around the longitudinal axis of the prosthesis, said meanders having apices alternately directed towards the proximal end and the distal end, second structural discrete elements extending along a series of parallel lines perpendicular to the longitudinal axis, the second structural discrete elements being individually arranged between two adjacent first structural elements and defining connecting struts by intersecting said two adjacent first structural elements, some of said second structural discrete elements showing either changes of slope with at least one shoulder, but no apices, or apices, but no shoulders, the second elements of a same line being preferably angularly shifted from the second elements of an adjacent line.

Another way to set out the main solution of the invention is to point out that the openings provided in the essentially cylindrical wall of the prosthesis are essentially "Z"-shaped both in the first state and the second state of the prosthesis and, at least in the expanded state, peripherally defined by eight apices where the cylindrical wall shows reversing of slope (or a "turning back" in the way for example of the apex of a zigzag).

A third way to set out said solution is to mention that the prosthesis of the invention has:

first structural elements having meanders extending essentially perpendicular to the axis of the implant, the first structural meanders having apices with reversings of slope alternately directed towards the proximal end and the distal end, two successive apices being connected together by connecting intermediate lengths so that the first structural meanders define a series of meandering cylinders staggered along the axis of the prosthesis, second and third structural discrete elements connecting two adjacent staggered meandering cylinders together, the second connecting structural discrete elements intersecting said adjacent staggered meandering cylinders at apices thereof, whereas the third connecting structural discrete elements intersect two adjacent staggered meandering cylinders at connecting intermediate lengths thereof.

In connection with said first and third ways of setting out the solution of the invention, it is advised:

that the second structural discrete elements which have points of reversing of slope, but no shoulders, intersect the adjacent first structural elements (or adjacent staggered meandering cylinders) at the apices thereof, whereas on the contrary, the third structural discrete elements which have at least one shoulder, but no reversings of slope, will advantageously intersect the first structural elements (or staggered meandering cylinders) at the intermediate lengths thereof, between two apices.

In connection with the above-mentioned problems, it will be noted that another characteristic of the invention advises that the second structural discrete elements, i.e. the second structural discrete elements substantially "zigzag"-shaped (having apices, but no shoulders) extend between adjacent first structural elements (or adjacent staggered meandering cylinders) over at least a portion of the height (or width) thereof, said characteristic allowing to control the size of the cells of the prosthesis, in particular in the radially open state of the prosthesis.

BRIEF DESCRIPTION OF THE SEVERAL VIEWS OF THE DRAWINGS

A more detailed description of the invention is given below in connection with appended drawings wherein.

DETAILED DESCRIPTION OF THE PREFERRED EMBODIMENTS

Figure 2:
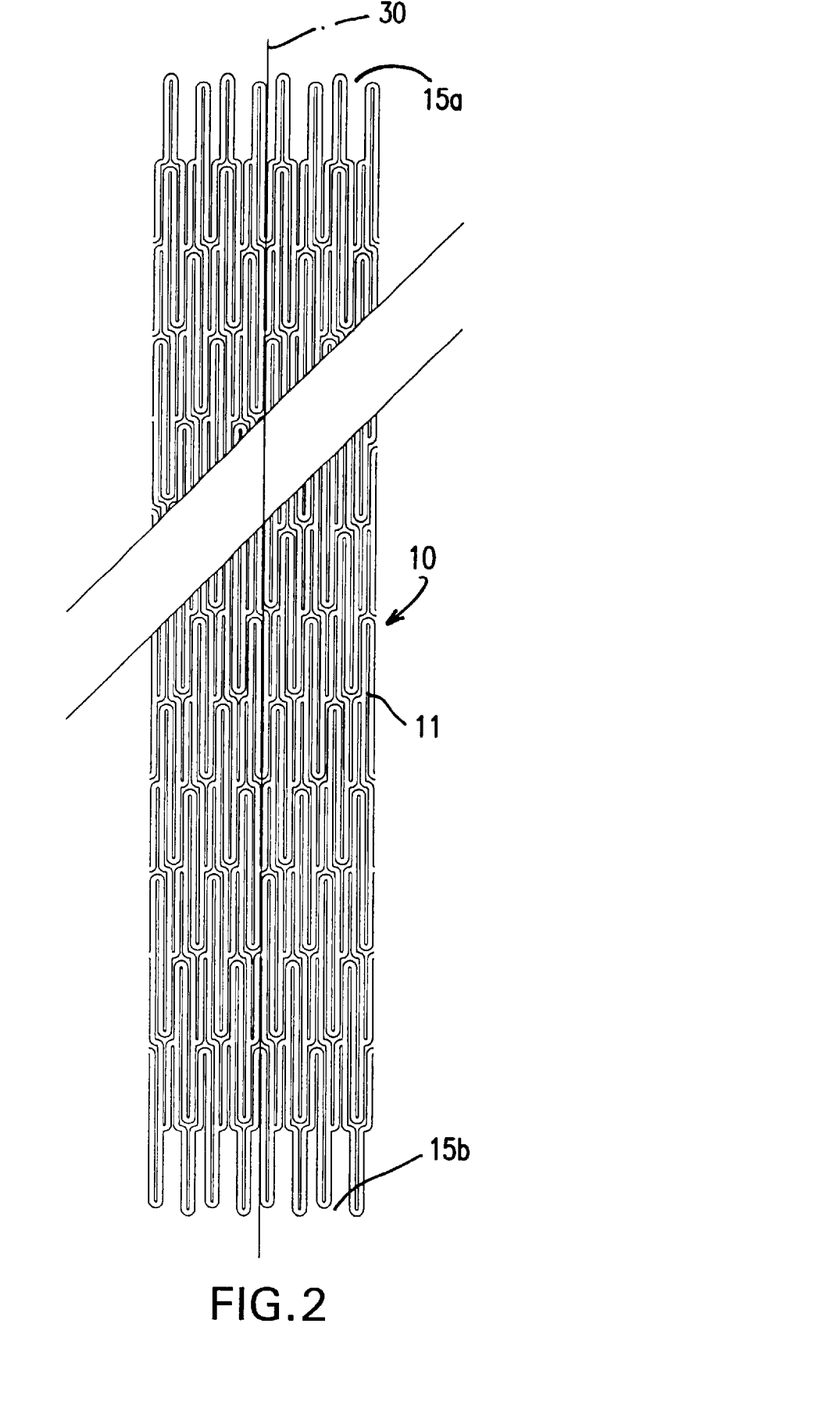
FIG. 2 shows a prosthesis (stent) according to the invention, in the radially restricted state.

On FIG. 2, one can see the global aspect of a stent 10 according to the invention. As a usual term, the term "stent" means a prosthesis intended to be implanted in an anatomical duct, such as a vessel. A stent is a support structure of the wall of said vessel (iliac vessel, in particular), which can be used as a widener, more particularly in case of a stenosis.

The prosthesis 10 has a longitudinal axis 30 along which the structure of the prosthesis extends. This structure has a tubular shape, particularly in the radially expanded state of the prosthesis.

On FIG. 2, the stent is in its radially restricted state, ready to be implanted in a human duct, in particular by the endoluminal way, for example by the technique called "SELDINGER".

The structure 11 is preferably metallic. It can be made of stainless steel or of a thermally shaped memory alloy (such as "NITINOL"®).

Figure 3:
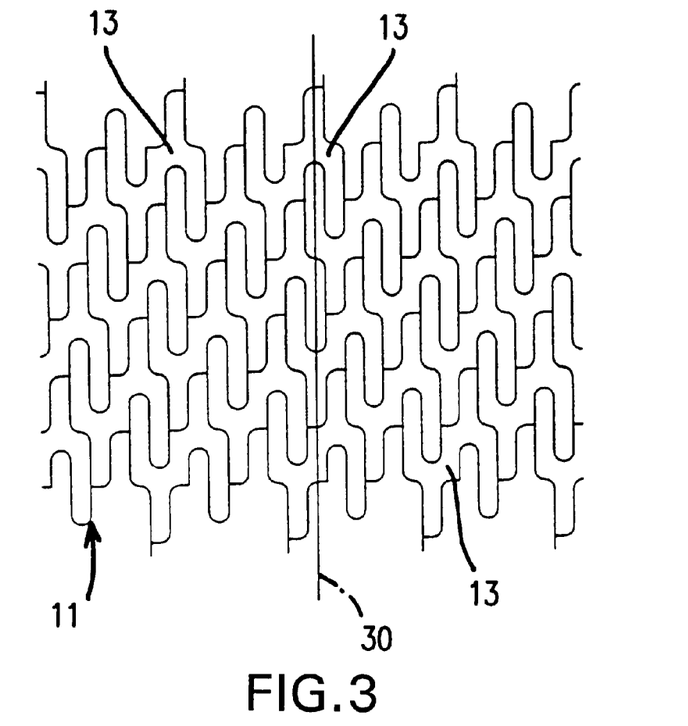
FIG. 3 illustrates, in a partial flat expanded view, the shape of the structure shown in FIG. 1, in a magnified view.

FIG. 3 shows in a magnified view, with another proportions, the drawing of the structure 11, the lines of which are parted for being more easily readable.

Structure 11 is a one-piece structure and has a series of cells or "openings", 13. One of these openings is illustrated on FIG. 4.

In the present case, all the cells of the structure are identical (except the cells at the two ends, respectively proximal, 15a, and distal, 15b, where all the angles are rounded).

Figure 4:
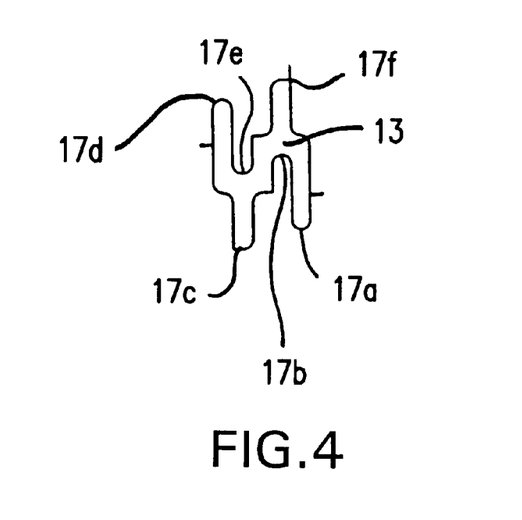
FIG. 4 shows a cell of the structure illustrated on FIG. 3.

FIGS. 3 and 4 clearly show the globally "Z" shape or "S" shape of each cell 13. Such a shape can be also seen on FIG. 5, where a magnified detail of the structure 11 is illustrated, in a state radially expanded round the longitudinal axis 30.

On FIGS. 3 and 4, each cell 13 is parametrically defined by six apices 17a, 17b, 17c, 17d, 17e, 17f, i.e. six zones of reversing of slope, or of "turning back", said six apices become eight in the radially expanded state (FIG. 5), the connecting sections of the cell with the adjacent cells creating two apices 17g,17h, the beginning of which can be seen on FIG. 4.

This "Z" shape of the cells is an advantage against the shape of the cells shown on FIG. 1, which is less regular due to the "doubled section" 5.

Figure 5:
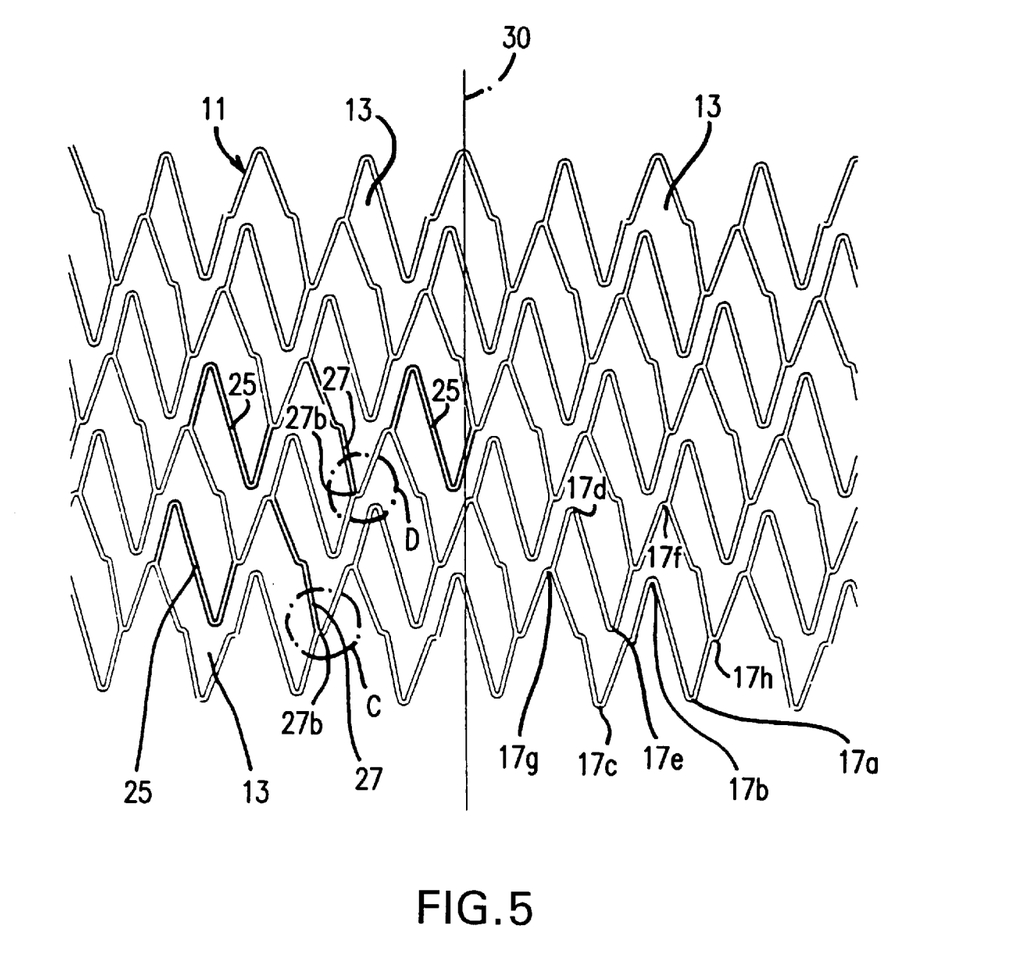
FIG. 5 illustrates, in a flat expanded view, a part of the prosthesis illustrated on FIG. 2.

On FIG. 5, it can be noticed that this doubled section does not exist, as shown at zones C and D, and this fact allows in particular, a more balanced radial opening of the prosthesis.

Compared to the cells of FIG. 1, cells of the implant of the invention have at least an apex less.

Figure 6:
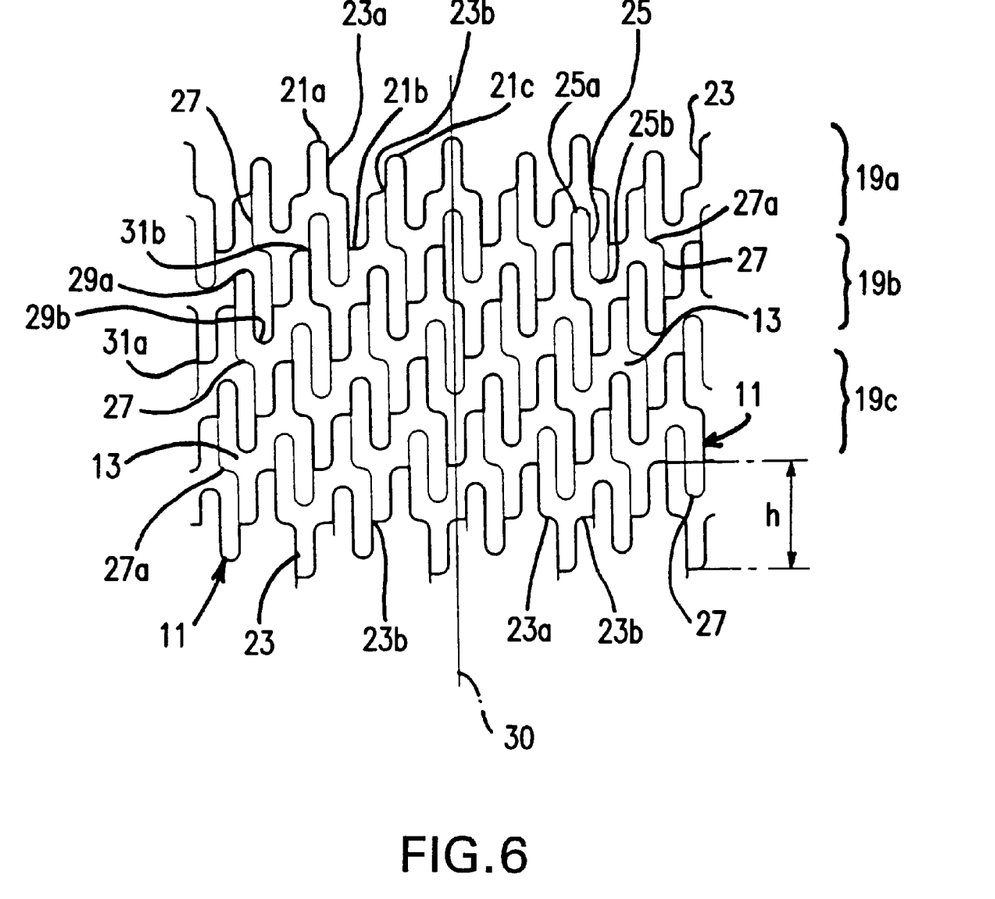
FIG. 6 shows the same structure as on FIG. 3, but with a stroke of the lines of the "helices-shaped" meanders.

On FIG. 6, is reinforced the stroke of the illustration of the meanders formed from the structural lines (here in a flat expanded view). Said structural lines extend perpendicular to the longitudinal axis 30, so that they define along said axis 30 a series of staggered meandering cylinders such as 19a,19b,19c (once said lines are each closed on themselves).

The meanders of each stage are formed from successive apices such as 21a, 21b, 21c successively connected two by two by connecting intermediate lengths such as 23a, 23b.

The meanders are identical from stage to stage, except at the two ends where all the apices are rounded.

These meanders are called "first staggered meandering cylinders" and are referenced at 23.

Figure 7:
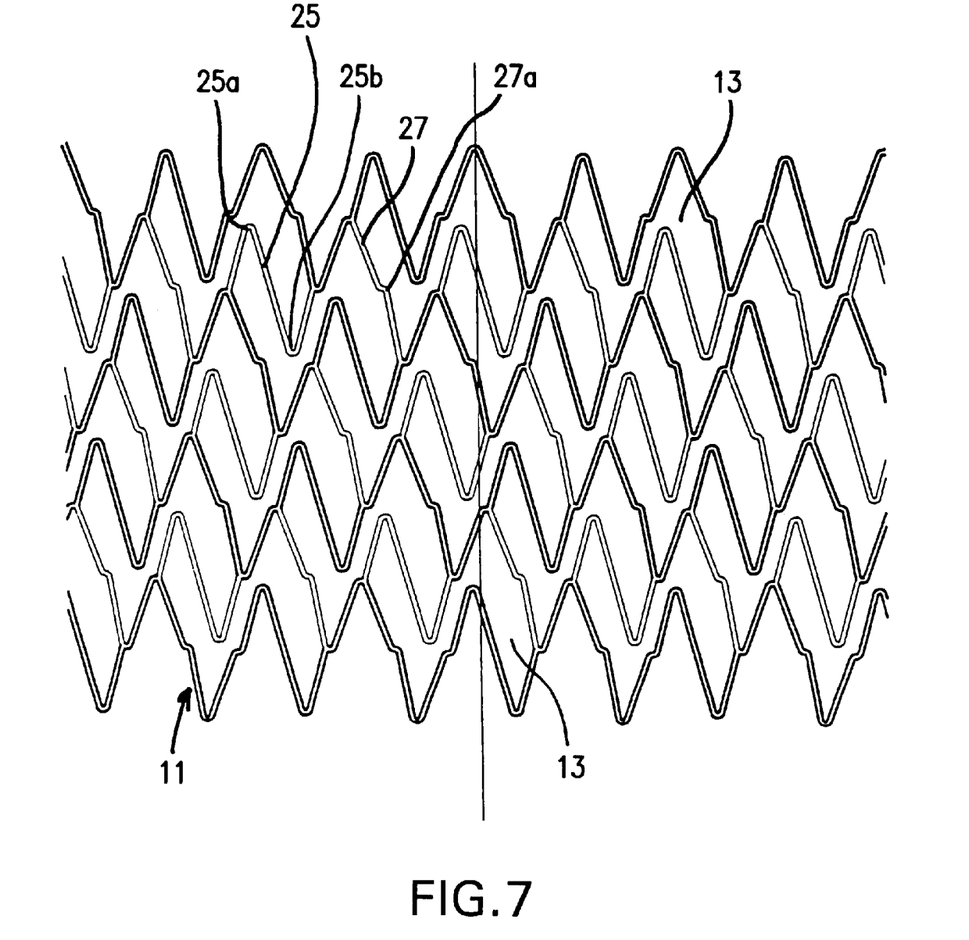
FIG. 7 is the same illustration as FIG. 5, but FIG. 7 shows the intensified lines of FIG. 6, And FIGS. 8, 9 and 10 show the same illustrations as FIGS. 3 and 6, but intensified lines show the meanders defining the <<helices>>.

On FIGS. 6 and 7, the meanders of two adjacent stages, such as 19a, 19b, are connected respectively by second and third connecting structural discrete elements.

Both in the radially restricted state and the radially expanded state, the second and third structural discrete elements, which are curved, have as only curvature areas, respectively two reversed apices 25a, 25b, and one shoulder 27a.

The second structural discrete elements have only rectilinear sections between two adjacent apices such as 25a, 25b, where slope of said structural discrete element is reversed in the way of a hairpin, successively towards the proximal end and towards the distal end.

Further, each third structural discrete element 27 has, substantially halflength, a rounded shoulder showing a change of slope, but no reversing of slope.

To obtain the substantially "Z"-shape of cells 13, the second structural discrete elements 25 (which are substantially "S"-shaped) are connected by their ends, at the opposite apices of the meandering cylinders which form two adjacent stages, whereas the ends of the third structural discrete elements are connected at intermediate zones between two successive apices of a same stage.

It must be clear that "opposite apices" means two apices directed respectively towards the proximal end and the distal end of the structure.

So, especially in the radially restricted state, apices are either directed towards the distal end or towards the proximal end of the prosthesis.

Furthermore, two lines of meanders defining two adjacent stages such as 19a, 19b are circumferentially shifted of each other, with a partial shift of phase.

It will be noted that the second structural discrete elements 25 intersect (or link up with one another) two "extreme" apices of meanders of two adjacent stages (i.e. the apices which are, in an axial direction like in the opposite one, the highest ones of the meanders, unlike for example the "less high" apices such as the rounded apices 29a, 29b), whereas the third structural discrete elements 27 intersect (at their ends) two axially adjacent meanders, at intermediate points of said meanders located between one of these "less high apices" and a following "high apex", such as 31b, or a previous "high apex", such as 31a (said "following apex" 31b and said "previous apex" 31a being located, on a common meander, on both sides of the above-mentioned "less high apices" 29a, 29b which are successively located along such a common meander).

In particular at the areas (or zones) shown by a reinforced stroke, the shape of the third structural discrete elements 27, and the connection of their lower end 27b to the corresponding meander, together with the shape and the location of the connecting points of the second structural discrete elements 25, as shown in particular on FIG. 5, favor the global balance of the prosthesis and the "Z"-shape of the cells 13.

Figure 8:
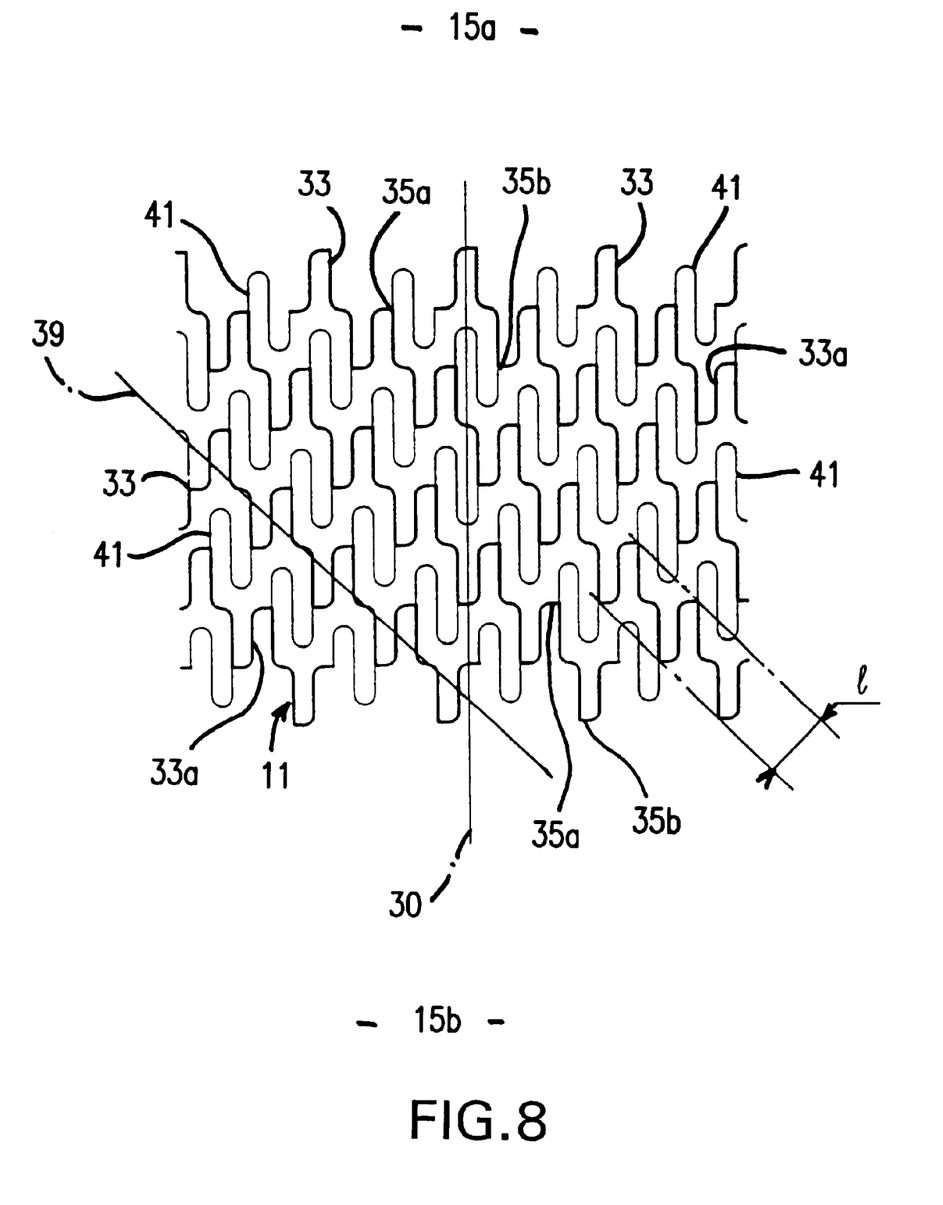
Figure 9:
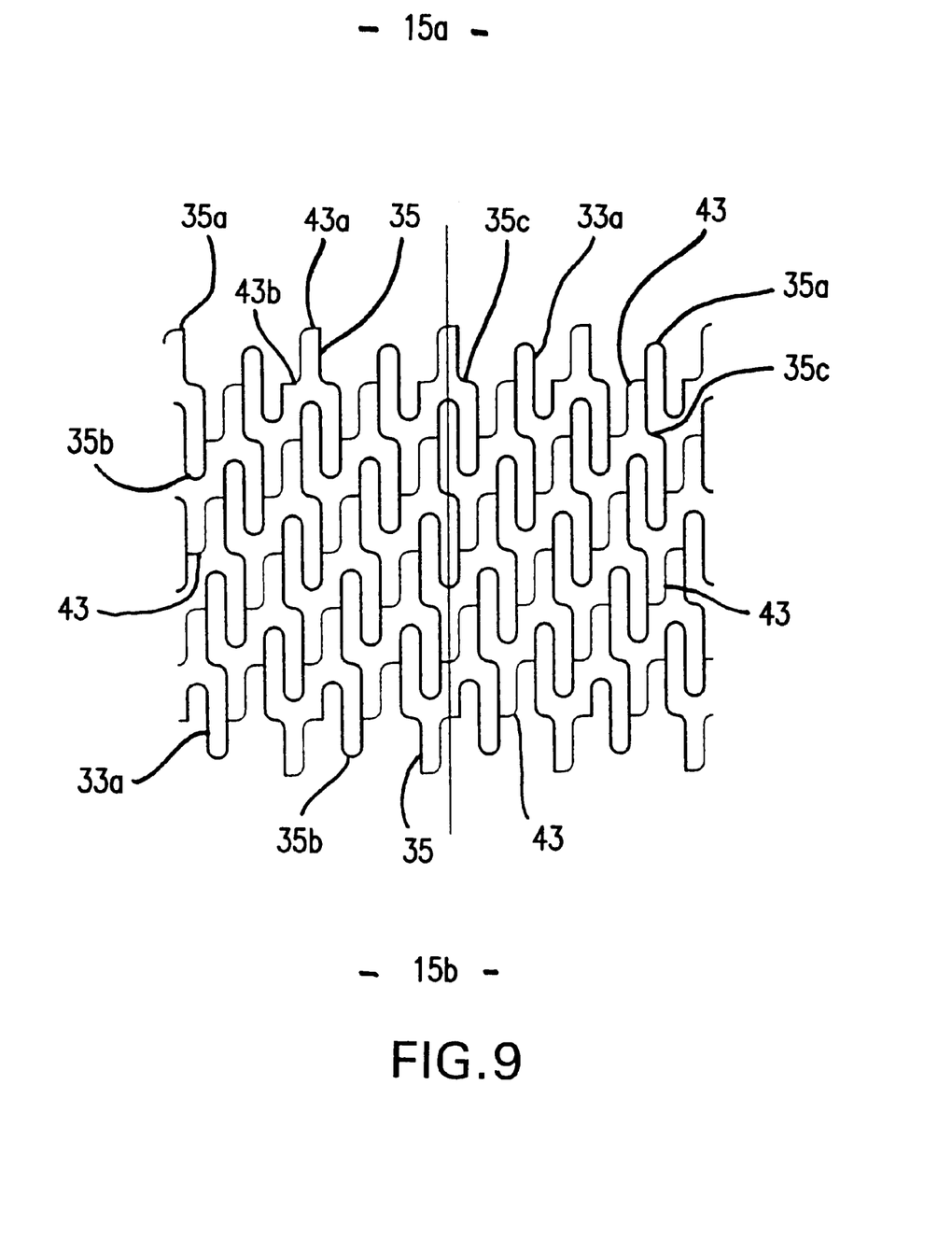
Figure 10:
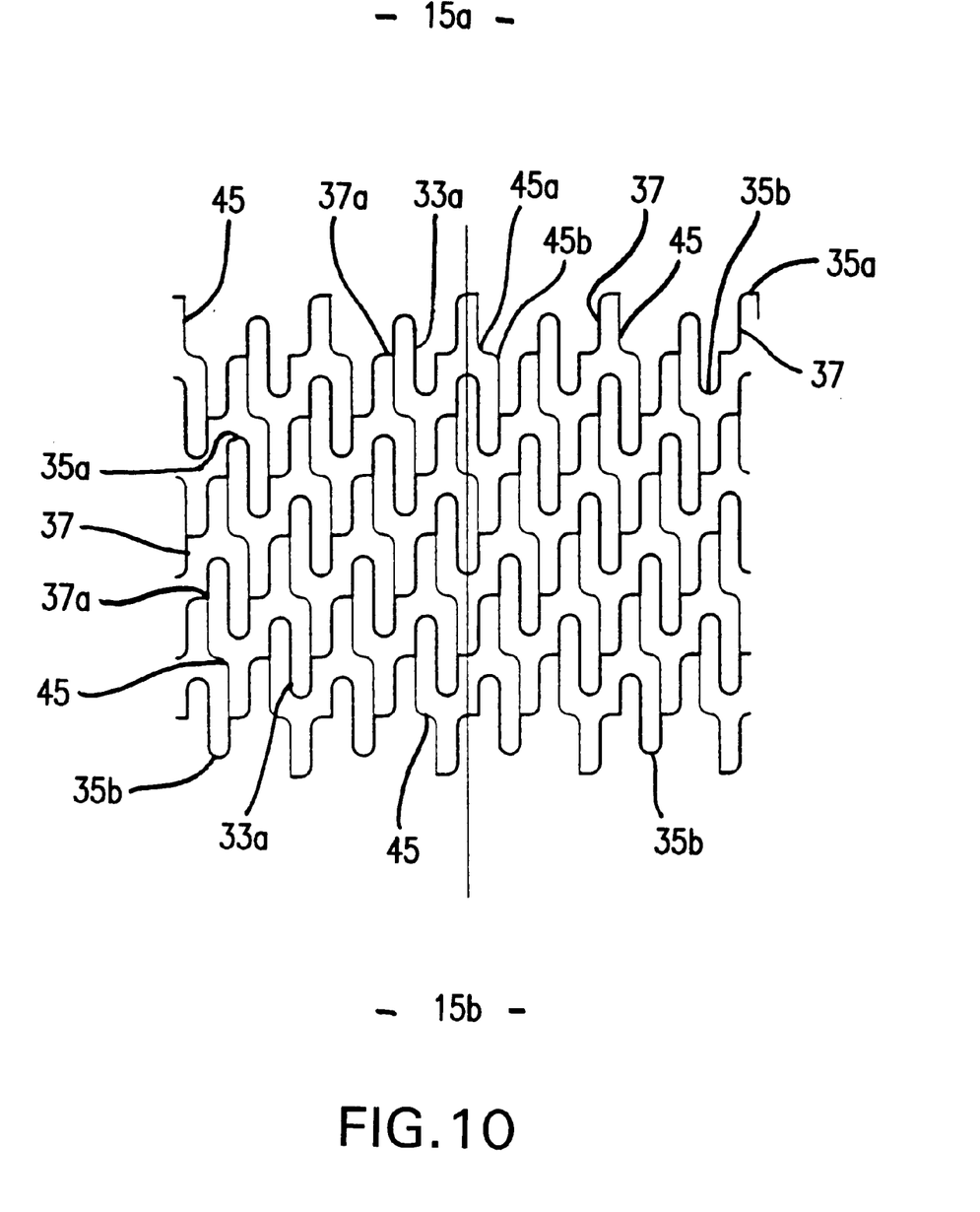

If one does not speak anymore about "cells" or about staggered cylinders substantially perpendicular to the axis 30, but if a longitudinal approach is followed, the vision that one can have of the structure 11 is still different, as shown in FIGS. 8, 9, 10 where is reinforced the stroke of the meanders which extend along a series of parallel helices round the axis 30.

On these figures the lines of meanders are successively referenced, 33 (FIG. 8), 35 (FIG. 9) and 37 (FIG. 10).

On FIG. 8, is referenced 39 one of the helix-shaped axes along which extends one of the lines of meanders 33 (once the structure is closed on itself).

Said meanders extending along a series of parallel helixes are called "first structural elements". Like the previous meanders, such as 23, they have a succession of apices connected together, two by two, by intermediate sections having a shoulder, for some of them, or no shoulders, for some others {see section 33a).

Of course, for forming the meanders, the successive apices are opposite: For example, the apex referenced 35a is axially directed towards the proximal end 15a, while the following apex 35b is axially directed towards the distal end 15b.

It will be noted once more the partial angular shift of the meanders on the circumference of the structure.

Further, the first structural elements of two adjacent lines are connected, two by two, by second structural discrete elements which intersect said first structural elements for forming the one-piece structure of the invention.

On FIGS. 8, 9, 10, the second elements are successively referenced 41, 43 and 45.

On FIG. 8, the second elements 41 have a "S" shape (rocked at 90°) showing two rounded apices substantially like hairpins (at least in the radially restricted state of the structure, as illustrated), like the "second structural discrete elements" 25 of FIG. 6 (which form the same filamentary sections). Said elements 41 are linked to reversed apices (such as 35a, 35b) of two adjacent lines of meanders 33.

On FIG. 9, the elements 43 have a warped "S" shape, but no apex, while showing two successive reversed bends. These reversed bends are rounded at substantially 90°, and are referenced 43a, 43b with reference to a determined section of said elements.

On FIG. 10, one can see the structural discrete elements 45 showing their substantially warped "S" aspect with two successive bends rounded at substantially 90° and referenced 45a, 45b (the "S" shape is rocked vertically, like on FIG. 8).

Said "second structural elements" 43 and 45 are linked to zones of meanders, respectively 35, 37, located between two successive reversed apices thereof.

Every element 43 intersects the concerned lines of meanders 35 at each end thereof, at a point located between an apex and an intermediate shoulder (such as 35c) of said meanders (FIG. 9).

Linking of ends of each element 45 is done at shoulders 37a located on the two concerned lines of meanders (FIG. 10).

A specific feature can also be noticed on FIGS. 8 to 10: Unlike the prior art (illustration of FIG. 1), no structural discrete element between the continuous meanders extending along a series of helices (33, 35, 37) has both shoulders (with therefore a rounded bump, such as 43a, 43b, 45a, 45b) and apices (with therefore a reversing of slope; element 41).

It will be also noticed that the above-mentioned second structural discrete elements 41, 43, 45, extend along a series of parallel lines, which also form helices coiled round the axis 30.

In an embodiment, said second structural discrete elements might be arranged along a series of parallel lines, but perpendicular to the axis 30, with a circumferential angular shift between two adjacent lines (arrangement substantially in quincunx).

On FIGS. 6 and 8, are respectively referenced 1 the width of a line of meanders 33 and h the height (parallel to the axis 30) of a line of meanders 23, in order to show that in every case, second connecting structural discrete elements (respectively 41 and 27) extend, between two meanders they link (or intersect), over a portion of the width (respectively height) of the meanders. As a consequence adapted size cells are obtained, with the sought shape. Warping (such as illustrated by FIG. 1) is further avoided.

What is claimed is:

1. A one-piece medical prosthesis implantable in an anatomical duct, in order to treat a disease of said duct, the prosthesis having:

a longitudinal axis, a first radially restricted state or a second radially expanded state, a proximal end and a distal end, first structural elements having meanders extending essentially perpendicular to the longitudinal axis, the first structural elements having first, high apices alternately directed towards the proximal end and the distal end, some of two successive of said first, high apices being separated by second, less high apices, two successive apices being connected together by connecting intermediate lengths so that said first structural elements define a series of meandering cylinders staggered along the longitudinal axis, second and third connecting structural discrete elements connecting two adjacent staggered meandering cylinders together, the second connecting structural discrete elements intersecting said adjacent staggered meandering cylinders at two adjacent, high apices thereof, respectively directed towards the proximal end and the distal end of the prosthesis, and, the third connecting structural discrete elements intersect two adjacent staggered meandering cylinders at connecting intermediate lengths thereof.

2. The medical prosthesis according to claim 1, wherein:

the second connecting structural discrete elements have apices showing reversings of slope defining alternate hairpins extending parallel to the longitudinal axis, and the third connecting structural discrete elements have at least one shoulder, but no apices.

3. The medical prosthesis according to claim 1, wherein:

each stage of the staggered meandering cylinders has a predetermined height along the longitudinal axis, and, the second connecting structural discrete elements extend between two adjacent staggered meandering cylinders, over only a portion of the predetermined height thereof.

4. A one-piece medical prosthesis implantable in an anatomical duct, in order to treat a disease of said duct, the prosthesis having:

a longitudinal axis, a first radially restricted state or a second radially expanded state, a proximal end and a distal end, first structural elements having meanders extending essentially perpendicular to the longitudinal axis, the first structural elements having first, high apices alternately directed towards the proximal end and the distal end, some of two successive of said first, high apices being separated by second, less high apices, two successive apices-being connected together by connecting intermediate lengths so that said first structural elements define a series of meandering cylinders staggered along the longitudinal axis, second and third connecting structural discrete elements connecting two adjacent staggered meandering cylinders together, the second connecting structural discrete elements intersect said adjacent staggered meandering cylinders at two adjacent, high apices thereof, respectively directed towards the proximal end and the distal end of the prosthesis, and, the third connecting structural discrete elements intersect two adjacent staggered meandering cylinders at connecting intermediate lengths thereof extending between one of said first, high apices and one of said second, less high,apices.

5. The medical prosthesis according to claim 4, wherein:

the second structural discrete elements show two curves, inverted from each other, so that they are individually "S"-shaped, the prosthesis is substantially tubular and comprises an essentially cylindrical wall through which said meanders and said second and third connecting structural discrete elements define openings, and, said openings are essentially "Z"-shaped both in the first state and the second state of the prosthesis, the openings being, in one of said first and second states, peripherally defined by at least six of said apices.

6. The medical prosthesis according to claim 5, wherein all the openings are identically shaped.

* * * * *